(12) United States Patent
Mooshofer

(10) Patent No.: US 9,989,500 B2
(45) Date of Patent: Jun. 5, 2018

(54) SAFT ANALYSIS OF DEFECTS CLOSE TO THE SURFACE

(71) Applicant: Siemens Aktiengesellschaft, Munich (DE)

(72) Inventor: Hubert Mooshofer, Munich (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 290 days.

(21) Appl. No.: 14/898,227

(22) PCT Filed: Jan. 16, 2014

(86) PCT No.: PCT/EP2014/050752
§ 371 (c)(1),
(2) Date: Dec. 14, 2015

(87) PCT Pub. No.: WO2014/198424
PCT Pub. Date: Dec. 18, 2014

(65) Prior Publication Data
US 2016/0146763 A1  May 26, 2016

(30) Foreign Application Priority Data

Jun. 13, 2013  (DE) .................. 10 2013 211 064

(51) Int. Cl.
*G01N 29/06* (2006.01)
*G01N 29/14* (2006.01)
*G01N 29/44* (2006.01)

(52) U.S. Cl.
CPC ........... *G01N 29/14* (2013.01); *G01N 29/069* (2013.01); *G01N 29/44* (2013.01); *G01N 2291/0234* (2013.01); *G01N 2291/044* (2013.01)

(58) Field of Classification Search
CPC ........... B22C 9/103; B22C 9/108; B22C 9/24; F01D 5/187; G01B 17/02; F05D 2220/32; F05D 2230/21; F05D 2260/20
(Continued)

(56) References Cited

U.S. PATENT DOCUMENTS 3,210,997 A * 10/1965 Karlby .................. G01F 1/1155
73/861.92
4,240,281 A * 12/1980 Lather .................... G01N 29/30
73/1.82
(Continued)

FOREIGN PATENT DOCUMENTS

DE   102005051783 A1   5/2007   ............. G01N 29/07
DE   102006003978 A1   8/2007   ............. G01N 29/06
(Continued)

OTHER PUBLICATIONS

Pudovikov, Sergey et al., "Quanitative Ultrasonic Sound Testing of Anisotrophic Materials Using Sampling Phased Array Technology" Fraunhofer Institute for Non-Destructive Evaluation, pp. 1-8 (German language w/ English abstract), 2010.
(Continued)

*Primary Examiner* — J M Saint Surin
(74) *Attorney, Agent, or Firm* — Slayden Grubert Beard PLLC

(57) ABSTRACT

A method and device for the ultrasonic testing of test objects by means of a test head. A computer device directly acquires, during a SAFT analysis for determining points in time of the amplitudes to be summed up from among the image time signals, a propagation time, which depends on the test head, from the test head positioned at a measuring point to the location of each of a plurality of voxels and uses the propagation time for calculating an amplitude total for the plurality of voxels.

20 Claims, 2 Drawing Sheets

(58) Field of Classification Search
USPC .......................................................... 73/596
See application file for complete search history.

(56) References Cited

U.S. PATENT DOCUMENTS

| | | | | |
|---|---|---|---|---|
| 4,252,068 | A * | 2/1981 | Nolan .................... | B61G 9/24 105/199.4 |
| 4,867,168 | A * | 9/1989 | Stoor ...................... | G09B 9/00 434/262 |
| 5,046,866 | A * | 9/1991 | Mulcahy ................ | B61F 5/14 384/423 |
| 5,820,774 | A * | 10/1998 | Dietrich ................. | B22C 9/10 164/369 |
| 6,019,001 | A * | 2/2000 | Schreiner .............. | G01N 29/27 73/618 |
| 6,347,660 | B1 * | 2/2002 | Sikkenga ............... | B22C 7/026 164/369 |
| 6,761,534 | B1 * | 7/2004 | Willett .................... | F01D 5/18 416/191 |
| 8,109,147 | B2 | 2/2012 | Kröning et al. ........... | 73/628 |
| 8,656,782 | B2 | 2/2014 | Boehm et al. .......... | 73/620 |
| 2004/0094287 | A1 * | 5/2004 | Wang ...................... | B22C 9/10 164/361 |
| 2005/0247429 | A1 * | 11/2005 | Turkington .......... | B22C 7/026 164/516 |
| 2009/0217764 | A1 | 9/2009 | Kröning et al. ........... | 73/628 |
| 2015/0323506 | A1 | 11/2015 | Goldammer et al. | |

FOREIGN PATENT DOCUMENTS

| | | | |
|---|---|---|---|
| DE | 102006059413 A1 | 6/2008 | ............. G01N 29/07 |
| DE | 102010040856 A1 | 3/2012 | ............. G01N 29/07 |
| EP | 2469276 A1 | 6/2012 | ............. G01N 29/06 |
| WO | 2014/198424 A1 | 12/2014 | ............. G01N 29/06 |

OTHER PUBLICATIONS

German Office Action, Application No. 102013211064.2, 5 pages, dated Feb. 13, 2014.
International Search Report and Written Opinion, Application No. PCT/EP2014/050752, 17 pages, dated Apr. 23, 2014.

* cited by examiner

SAFT ANALYSIS OF DEFECTS CLOSE TO THE SURFACE

CROSS-REFERENCE TO RELATED APPLICATIONS

This application is a U.S. National Stage Application of International Application No. PCT/EP2014/050752 filed Jan. 16, 2014, which designates the United States of America, and claims priority to DE Application No. 10 2013 211 064.2 filed Jun. 13, 2013, the contents of which are hereby incorporated by reference in their entirety.

TECHNICAL FIELD

The present invention relates to a method and a device for the ultrasonic testing of test objects, in particular metallic components, by means of a synthetic aperture focusing technique (SAFT) analysis.

BACKGROUND

Defects, in particular in metallic components, for example, in forged products, are detected by means of ultrasonic testing. The analysis technique SAFT is known for better localization and separation of defects.

SAFT (synthetic aperture focusing technique) or synthetic aperture method refers to a method in which a B-image is obtained by computer from previously recorded, digitized, and stored A-images. A test head having the largest possible aperture angle is moved along a line. A-images are digitized at intervals and stored in a computer in this case. Depending on the test head position, echoes of a flaw occur with corresponding runtime differences. For each voxel of the test volume of a workpiece, sound runtimes to be expected are conventionally calculated from geometric relationships for each test head position and the echo amplitudes corresponding to these runtimes are searched out and totaled in the stored A-images. This results in exact runtime compensation at the location of a flaw, so that the flaw echoes are superimposed there in-phase from all test head positions and result in a correspondingly high computed amplitude. The sound intensity is therefore focused on the respective observed voxel. If the obtained amplitude value is associated with each voxel in the case of such synthetic focusing, a focused volume data set is obtained.

The inspection is performed in this case in a conventional manner, however, the HF data and the precise items of position information are recorded. During the subsequent SAFT analysis of the measurement data, amplitude totals are calculated from many time signals, the so-called A-images, in each case for small elements of the volume to be tested. Such elements of the volume to be tested are referred to as voxels. Corresponding to the respective distance between voxel and measurement point, which is the position of the test head, the amplitudes are totaled at the points in time which correspond to the respective distance of voxel to measurement point.

As a result of the aperture angle of the sound bundle emitted from the test head, defect indications are spatially blurred, so that in the sectional view, the so-called B-image, the punctiform defects become sickle-shaped indications. These sickle-shaped indications are again concentrated on punctiform indications by means of the SAFT analysis.

However, this functions only in the so-called far field; other indication shapes result in the vicinity of the test subject surface due to the test head sound field. Therefore, conventional SAFT analysis achieves poor results in the vicinity of the test surface.

Different variants of the SAFT algorithm are known, which are oriented on other problems and do not cause any improvement in the near field, however. Thus, for example, for accelerating the calculation, FT-SAFT analysis is known, which causes a significant speed advantage by using the Fourier transform for planar test surfaces. Furthermore, for testing homogeneous anisotropic materials, the HAFT-SAFT method is known, in which the direction-dependent propagation speed is taken into consideration. Instead of a spherical wave, the energy speed surfaces of a point wave depending on the respective materials are used as the basis.

SUMMARY

One embodiment provides a method for ultrasonic testing of test objects, in particular metallic components, by means of a test head, wherein in an SAFT analysis, a calculation of amplitude totals is executed in each case for elements of a volume to be tested of the test object from a number of A-image time signals, wherein, to determine points in time of the amplitudes to be totaled in the A-image time signals, a sound runtime, which is dependent on the test head, from the test head positioned at a measurement point to the location of the element of the volume to be tested is directly acquired and used.

In a further embodiment, the sound runtime is determined by means of analysis of a sound field simulation of the test head for the respective material of the test object.

In a further embodiment, the surface shape of the test object is taken into consideration in the sound field simulation.

In a further embodiment, an exact shape and an aperture allocation of an oscillator of the test head are taken into consideration in the sound field simulation.

In a further embodiment, a focusing of the test head is taken into consideration in the sound field simulation.

In a further embodiment, a delay according to a delay law is taken into consideration in the sound field simulation in the case of phased arrays.

In a further embodiment, the sound field simulation is monochromatic or polychromatic.

In a further embodiment, the sound field simulation is executed by means of a point source synthesis or in a spatially-discrete manner.

In a further embodiment, sound runtimes of the sound field simulation are determined beforehand, tabulated, and stored in retrievable form.

In a further embodiment, sound runtimes are acquired beforehand, tabulated, and stored in retrievable form by means of measurement of a sound field of the test head for the respective material of the test object.

In a further embodiment, tabulated sound runtimes for a plurality of test heads are stored in retrievable form in a test head library.

In a further embodiment, respective sound runtimes are interpolated from tabulated runtimes.

A further embodiment provides a device for ultrasonic testing of test objects, in particular metallic components, by means of a test head, wherein by means of a computer unit in an SAFT analysis, a calculation of amplitude totals is executed in each case for elements of a volume to be tested of the test object from a number of A-image time signals, wherein the computer unit directly acquires and uses a sound runtime, which is dependent on the test head, from the test head positioned at a measurement point to the location of the element of the volume to be tested for determining points in time of the amplitudes to be totaled in the A-image time signals.

In a further embodiment, the computer unit determines the sound runtime by means of analysis of a sound field simulation of the test head for the respective material of the test object.

In a further embodiment, the computer unit takes the surface shape of the test object into consideration in the sound field simulation.

In a further embodiment, the computer unit takes an exact shape and an aperture allocation of an oscillator of the test head into consideration in the sound field simulation.

In a further embodiment, the computer unit takes a focusing of the test head into consideration in the sound field simulation.

In a further embodiment, the computer unit takes a delay according to a delay law into consideration in the sound field simulation in the case of phased arrays.

In a further embodiment, the computer unit executes the sound field simulation in a monochromatic or polychromatic manner.

In a further embodiment, the computer unit executes the sound field simulation by means of a point source synthesis or in a spatially-discrete manner.

In a further embodiment, the computer unit determines sound runtimes of the sound field simulation beforehand and tabulates them and the table is stored in a retrievable manner by means of a storage unit.

In a further embodiment, a measuring unit acquires sound runtimes beforehand by means of measurement of a sound field of the test head for the respective material of the test object, a computer unit tabulates the measured sound runtimes, and a storage unit stores the table in retrievable form.

In a further embodiment, the tabulated sound runtimes are stored in a retrievable manner by means of the storage unit for a plurality of test heads in a test head library.

In a further embodiment, the computer unit interpolates respective sound runtimes from tabulated runtimes.

BRIEF DESCRIPTION OF THE DRAWINGS

Embodiments of the invention are described in greater detail below with reference to the figures, in which.

DETAILED DESCRIPTION

Figure 1:
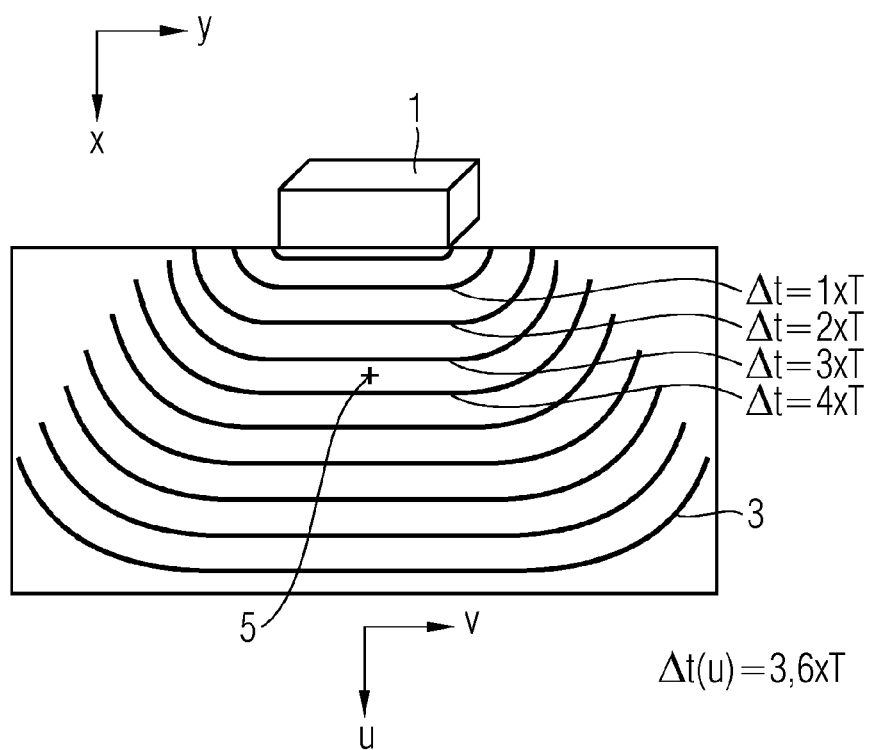
FIG. 1 shows an exemplary embodiment of a method according to the invention.

Embodiments of the present invention provide a method and a device for ultrasonic testing of test objects, in particular metallic components, by means of an analysis, in particular SAFT analysis, such that, in comparison to the prior art, better results are caused of the SAFT calculation in the vicinity of the surface of a test object, in particular better defect localization, stronger defect separation, and higher signal-to-noise ratio. Improved testing of test objects having small transverse dimensions, improved analysis of surface-proximal defects, and improved analysis if large or focused test heads are used are to be executable.

Some embodiments provide a method for ultrasonic testing of test objects, in particular metallic components, by means of a test head, wherein during an analysis, in particular an SAFT analysis, a calculation of amplitude totals is executed in each case for elements of a volume to be tested of the test object from a number of A-image time signals, wherein to determine points in time of the amplitudes to be totaled in the A-image time signals, a sound runtime, which is dependent on the test head, from the test head positioned at a measurement point to the location of the element of the volume to be tested is directly acquired and used.

Other embodiments provide a device for ultrasonic testing of the test object, in particular metallic components, by means of a test head, wherein by means of a computer unit in an analysis, in particular an SAFT analysis, a calculation of amplitude totals is executed in each case for elements of a volume to be tested of the test object from a number of A-image time signals, wherein the computer unit directly acquires and uses a sound runtime, which is dependent on the test head, from the test positioned at a measurement point to the location of the element of the volume to be tested for determining points in time of the amplitudes to be totaled in the A-image time signals.

In particular imaging ultrasonic testing fundamentally comprises all graphic modes of display of an acquired amplitude as a function of the time or the location. It extends from simple HF image display by means of a simple oscillograph via the A-image up to a D-image. Such ultrasonic images differ in the informative content thereof depending on the display. In this case, the A-image (and to a lesser extent the HF image) receives particular significance because of its display, which is comparatively simple to interpret. The ultrasonic testing is usually executed as a single-point test for physical reasons, the signals of which are processed as the A-image, which can be a non-rectified HF image, for example. A-images can be non-rectified or rectified. Only later in development history did the line scan (B-image) and the area scan (C/D-image) become technically usable. The scan is scanning in this case, because the A-images are assembled as lines or areas into an image and are scaled (for example, according to color or grayscale).

During a measurement, the HF signals are registered as a function of the location and the time, and are analyzed with respect to the signal runtime and/or the amplitude or damping.

During the SAFT analysis—in contrast to the conventional use of the distance between measurement point and voxel—the sound runtime as a function of the test head from a test head placed at the measurement point to the location of the voxel is taken into consideration, to determine the points in time of the amplitudes to be totaled in the A-image time signals. The determination of the sound runtime as a function of the test head can be performed in different ways in this case.

The sound runtimes are not derived indirectly from geometric variables, but rather are incorporated after the direct measurement thereof directly into the establishment of the amplitudes to be totaled in the amplitude-time curves of the A-image time signals.

Further advantageous embodiments are claimed in conjunction with the dependent claims.

According to one embodiment, the sound runtime can be determined by means of analysis of a sound field simulation of the test head for the respective material of the test object. By taking into consideration the sound field shape of the test head/test heads used during the SAFT analysis, the analysis in the vicinity of the test surface is improved.

According to a further embodiment, the surface shape of the test object can be taken into consideration in the sound field simulation.

According to a further embodiment, an exact shape and an aperture allocation of an oscillator of the test head can be taken into consideration in the sound field simulation.

According to a further embodiment, a focusing of the test head can be taken into consideration in the sound field simulation.

According to a further embodiment, a delay according to the delay law can be taken into consideration in the sound field simulation in the case of phased arrays.

According to a further embodiment, the sound field simulation can be monochromatic or polychromatic.

According to a further embodiment, the sound field simulation can be executed by means of a point source synthesis or in a spatially-discrete manner. Examples are FE, EFIT, and the like. FE is a conventional finite element method. EFIT is a conventional method referred to as the elastodynamic finite integration technique.

According to a further embodiment, sound runtimes of the sound field simulation can be determined beforehand, tabulated, and stored in a retrievable manner.

A performance of the sound field simulation can be executed beforehand and tabulation of the results can be performed thereafter.

According to a further embodiment, sound runtimes can be acquired beforehand, tabulated, and stored in retrievable form by means of measurement of a sound field of the test head for the respective material of the test head.

A determination of the sound field can be performed by measurement and a tabulation of the results can be executed thereafter.

According to a further embodiment, tabulated sound runtimes for a plurality of test heads can be stored in retrievable form in a test head library.

A performance of the sound field simulation can be executed for many test heads and storage of the sound runtimes can be performed in a test head library.

According to a further embodiment, respective sound runtimes can be interpolated from tabulated runtimes. An interpolation of the sound runtime from the measurement point to the voxel can be executed from the tabulated runtimes.

FIG. 1 shows an exemplary embodiment of a method according to the invention. FIG. 1 shows wavefronts in the near field of a test head 1, wherein runtimes $\Delta t$ are indicated as a multiple of a base duration or period T. According to embodiments of the present invention, better results of the SAFT calculation are caused in the vicinity of the test surface, in particular better defect localization, stronger defect separation, and greater NNR. This results in improved testing of objects 3 having small transverse dimensions, improved analysis of defects 5 close to the surface as a result of direct incident sound and shorter sound paths, and improved analysis upon the use of large test heads 1, for example, to introduce more signal energy into the test object 3, or upon the use of focused test heads. FIG. 1 shows ultrasonic waves propagating in pulses from the test head 1, which each generate a wavefront at integer multiples of a period T in the near field of the test head 1. A position of a defect 5 can be specified and established in this example as a sound runtime $\Delta t = 3.6 \times T$. In general, $\Delta t$ is dependent on all coordinates u, v, w. In principle, the function $\Delta t$ (u, v, w) applies. In contrast to conventional methods, the position of the defect is expressed directly as the sound runtime $\Delta t$, and an amplitude, which is provided for summation, of an A-image time signal is established thereby, in particular in the case of an SAFT analysis.

Figure 2:
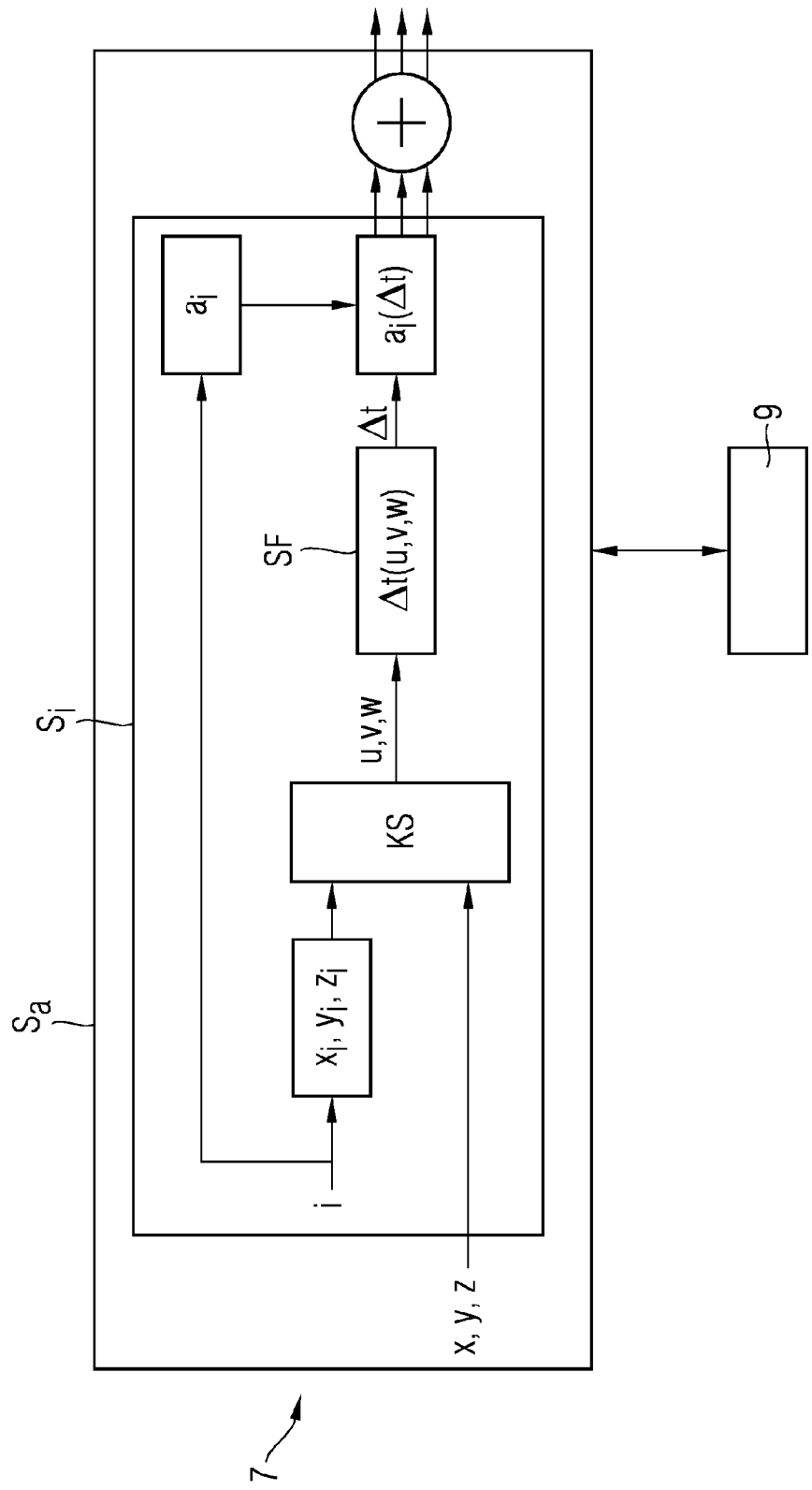
FIG. 2 shows an exemplary embodiment of a device according to the invention.

FIG. 2 shows an exemplary embodiment of a device according to the invention, which executes a method according to FIG. 1. By means of a test head 1 and a measuring unit, sound runtimes $\Delta t$ can be acquired beforehand by means of measurement of a sound field of the test head 1 for the respective material of the test head 3.

By means of a computer unit 7, in an SAFT analysis, a calculation of amplitude totals "+" can be executed in each case for voxels of the test object 3 from a number of A-image time signals, wherein the computer unit 7, for determining points in time $\Delta t$ of the amplitudes $a_i$ ($\Delta t$) to be totaled in the measured A-image time signals $a_i$, uses a sound runtime $\Delta t$, which is dependent on the test head 1, from the test head 1 positioned at a respective measurement point i ($x_i$, $y_i$, $z_i$) to the location of the voxel or defect 5. By means of the computer unit 7, the sound runtimes $\Delta t$ can be determined, for example, by means of analysis of a sound field simulation of the test head 1 for the respective material of the test object 3. The computer unit 7 can acquire sound runtimes $\Delta t$ in tabular form and the resulting tables can be stored in a retrievable manner by means of a storage unit 9. In FIG. 2, an external loop Sa via reconstructed positions x, y, z and an internal loop Si via measurement positions i are shown. A coordinate system transformation KS is performed into u, v, w coordinates. Corresponding sound runtimes $\Delta t$ are generated from u, v, w coordinates by means of the sound field SF of the test head 1. FIG. 1 depicts the illustration of the u coordinate of the defect 5 in the object 3 as the sound runtime $\Delta t$ (u).

The invention relates to a method and a device for ultrasonic testing of test objects by means of a test head, wherein by means of a computer unit in an SAFT analysis, a sound runtime, which is dependent on the test head, from the test head positioned on a measurement point to the location of the voxel is acquired directly and used for determining points in time of the amplitudes to be totaled in the A-image time signals.

What is claimed is:

1. A method for ultrasonic testing of a test object using a test head, the method comprising:
   emitting ultrasonic pulses by the test heat;
   for each of a plurality of volume elements of a test volume of the test object:
      determining a sound runtime from the test head positioned at a measurement point to a location of the respective volume element; and
      determining a point in time of an amplitude of an A-image time signal for the respective volume element based on the sound runtime determined for that respective volume element; and
   performing a SAFT analysis, including calculating an amplitude total for each of the plurality of volume elements of the test volume, based on the amplitudes of the A-image time signals for the plurality of volume elements;
   wherein each sound runtime is determined by analyzing a sound field simulation of the test head for a material of the test object; and
   the sound field simulation accounts for an exact shape and an aperture allocation of an oscillator of the test head.

2. The method of claim 1, wherein the sound field simulation accounts for a surface shape of the test object.

3. The method of claim 1, wherein the sound field simulation accounts for a focusing of the test head.

4. The method of claim 1, wherein the sound field simulation accounts for a delay according to a delay law for a phased array.

5. The method of claim 1, wherein the sound field simulation is monochromatic or polychromatic.

6. The method of claim 1, wherein the sound field simulation is executed by a point source synthesis or in a spatially-discrete manner.

7. The method of claim 1, further comprising determining and storing sound runtimes of the sound field simulation prior to the emitting of ultrasonic pulses by the test head.

8. The method of claim 7, wherein the sound runtimes are determined by measuring a sound field of the test head for the respective material of the test object.

9. The method of claim 7, comprising storing sound runtimes for a plurality of test heads in a test head library.

10. The method of claim 7, comprising interpolating particular sound runtimes from other stored runtimes.

11. A device for ultrasonic testing of a test object, comprising:
a test head, and
a computer unit comprising instructions stored in non-transitory computer-readable medium and executable by a processor to:
cause the test head to emit ultrasonic pulses by the test head,
for each a plurality of volume elements of a test volume of the test object:
determine a sound runtime from the test head positioned at a measurement point to a location of the respective volume element, as a function of the test head, and
determine a point in time of an amplitude of an A-image time signal for the respective volume element based on the sound runtime determined for that volume element, and
perform a SAFT analysis, including calculating an amplitude total for the plurality of volume elements of the test volume, based on the amplitudes of the A-image time signals for the plurality of volume elements;

wherein each sound runtime is determined by analyzing a sound field simulation of the test head for a material of the test object; and
the sound field simulation accounts for an exact shape and an aperture allocation of an oscillator of the test head.

12. The device of claim 11, wherein the computer unit accounts for a surface shape of the test object in the sound field simulation.

13. The device of claim 11, wherein the computer unit accounts for a focusing of the test head in the sound field simulation.

14. The device of claim 11, wherein for a phased array, the computer unit accounts for a delay according to a delay law in the sound field simulation.

15. The device of claim 11, wherein the computer unit executes the sound field simulation in a monochromatic or polychromatic manner.

16. The device of claim 11, wherein the computer unit executes the sound field simulation by a point source synthesis or in a spatially-discrete manner.

17. The device of claim 11, wherein the computer unit determines and stores in a storage unit sound runtimes of the sound field simulation prior to emitting ultrasonic pulses by the test head.

18. The device of claim 17, wherein the storage unit stores a test library including tabulated sound runtimes for a plurality of test heads.

19. The device of claim 18, wherein the computer unit is configured to interpolate respective sound runtimes from stored tabulated runtimes.

20. The device of claim 11, comprising a measuring unit configured to acquire sound runtimes by measuring a sound field of the test head for a material of the test object, and the computer unit tabulates the measured sound runtimes and stores the tabulated sound runtimes in the storage unit in retrievable form.

* * * * *